United States Patent [19]

Meier et al.

[11] Patent Number: 4,670,651

[45] Date of Patent: Jun. 2, 1987

[54] APPARATUS FOR PERFORMING THE SNMS METHOD

[75] Inventors: Stefan Meier, Cologne; Karl-Heinz Müller, Heltersberg, both of Fed. Rep. of Germany

[73] Assignee: Leybold-Heraeus GmbH, Cologne, Fed. Rep. of Germany

[21] Appl. No.: 779,868

[22] Filed: Sep. 25, 1985

[30] Foreign Application Priority Data

Sep. 27, 1984 [EP] European Pat. Off. ........... 84111519

[51] Int. Cl.⁴ .......................................... H01J 37/252
[52] U.S. Cl. ..................................... 250/309; 250/281
[58] Field of Search ........................ 250/281, 282, 309

[56] References Cited

U.S. PATENT DOCUMENTS 4,310,759 1/1982 Oechsner ........................... 250/309
4,447,724 5/1984 Oechsner ........................... 250/309

Primary Examiner—Bruce C. Anderson
Assistant Examiner—Jack I. Berman
Attorney, Agent, or Firm—Felfe & Lynch

[57] ABSTRACT

An apparatus for the performance of the SNMS process, having a separate ion source, a sample holder, a system for the production of a radio-frequency plasma and a mass analyzer, in which the ion source and the mass analyzer are disposed side by side on the same side of the chamber provided for the radio-frequency plasma, and in which the sample mounted on the sample holder is situated within the chamber provided for the radio-frequency plasma. This apparatus can be used not only for the performance of the two kinds of SNMS operation (DMB and SBM) but also secondary ion mass spectroscopy (SIMS) under optimum spatial conditions.

9 Claims, 3 Drawing Figures

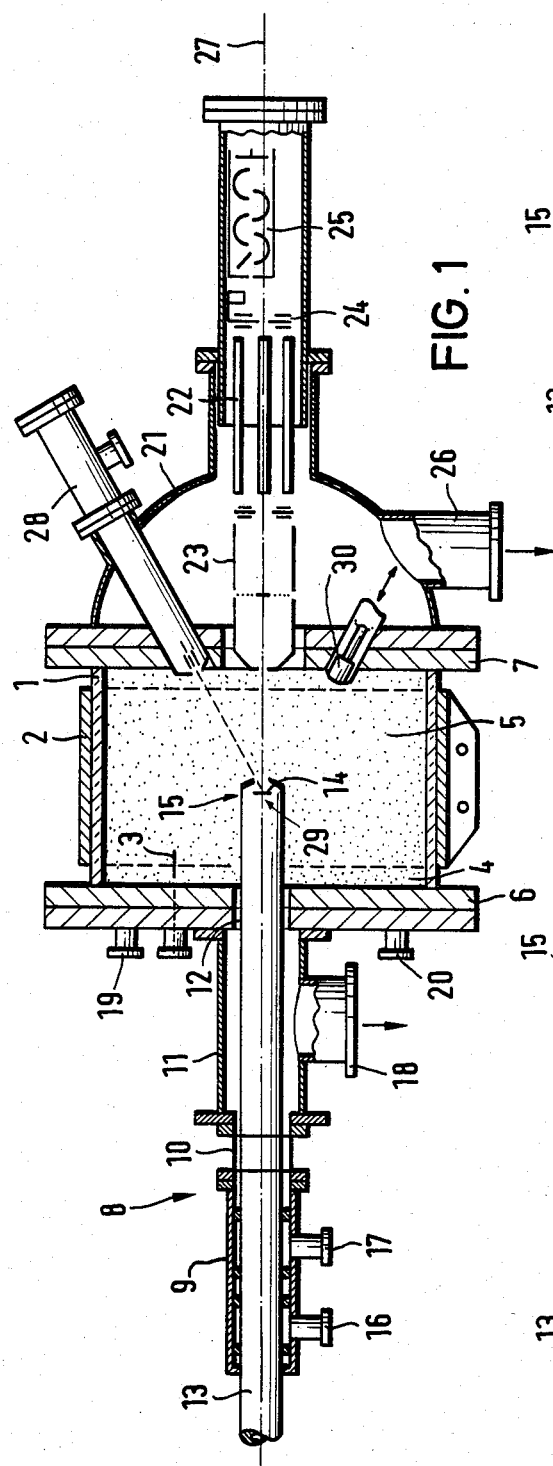
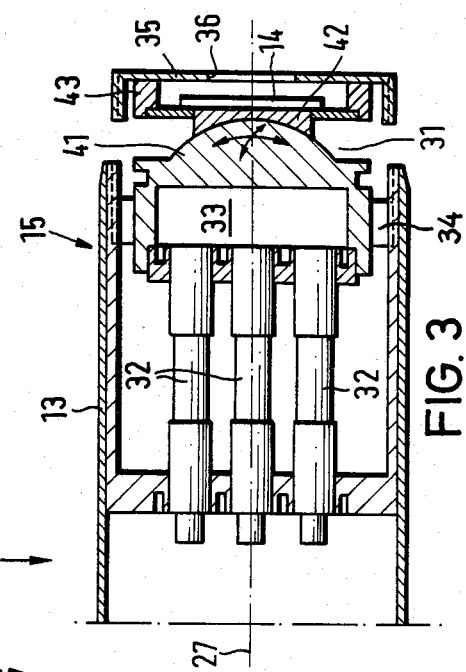
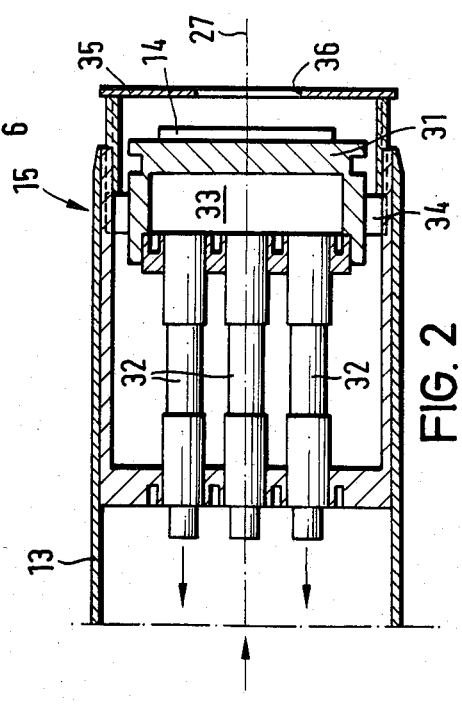

APPARATUS FOR PERFORMING THE SNMS METHOD

The invention relates to an apparatus for performing the SNMS method, having a separate ion source, a sample holder, a system for producing a radiofrequency plasma, and a mass analyzer.

In the so-called SNMS method (Sputtered or Secondary Neutral Mass Spectrometry) the analysis of a sample is performed by releasing neutral particles out of a sample surface by ion bombardment, ionizing the particles in a radiofrequency plasma, and then examining them by mass spectrometry. There are two ways of producing the primary ions.

In the one case there is the possibility of performing the bombardment of the sample with ions from the plasma (direct bombardment mode, DBM). For this purpose it is necessary to dispose the sample in range of the plasma and apply the voltage difference necessary for the desired bombardment between the radiofrequency plasma and the sample. This DBM/SNMS method has been published in Appl. Phys. 14, 43-47 (1977). This process can be used with conductive and semiconductive samples. In the case of nonconductors, however, no ion bombardment can be produced by applying a sample potential, as described in the above-cited publication.

Another possibilty consists of providing a separate ion source for bombarding the sample, so as to separate the primary ion generation from the post-ionization of the neutral particles by the radiofrequency plasma. This SBM (separate bombardment mode) mode of operation of the SNMS process is disclosed in DE-OS No. 29 50 330. In the apparatus described therein for the performance of this process, the separate ion source and the sample are disposed on one side of the radiofrequency plasma and the mass analyzer on the other side of the plasma. Between the sample and the radiofrequency plasma is a diaphragm consisting of a plurality of masks. This has the purpose on the one hand of preventing the impingement of ions and electrons from the plasma on the sample. On the other hand it is intended to prevent the passage of secondary ions released directly from the sample by the ion bombardment, since these are undesirable in the SNMS method and can form a disturbing background. With this known apparatus nonconductors can be tested only if charges produced by the ion bombardment are compensated.

A disadvantage of the formerly known apparatus is that they are not suitable for comparative measurements by the DBM/SNMS process on the one hand, and by the SBM/SNMS process on the other. In changing over from one type of SNMS operation to the other, either expensive conversions of the apparatus are necessary, or else different apparatus are needed.

The present invention is addressed to the problem of creating an apparatus of the kind specified in the beginning, whereby a sample can be analyzed both by the DBM/SNMS process and by the SBM/SNMS process in direct succession to one another.

This problem is solved according to the invention in that the ion source and the mass analyzer are arranged side by side on the same side of the space provided for the radiofrequency plasma, and that the sample mounted on the sample holder is situated within the space provided for the radiofrequency plasma. In the performance of the DBM/SNMS process, the ion source remains shut off.

The voltage necessary for the bombardment of the sample with ions from the plasma is applied between the radiofrequency plasma—preferably an argon plasma—and the sample or its sample holder. In the case of conductors and semiconductors it can be a DC voltage. In the case of nonconductors a radiofrequency AC voltage is applied to the sample base. On account of the dielectric properties of the nonconductor and the different mobilities of the ions and electrons in the plasma, a negative DC potential lies on the surface of the nonconductor, which in turn leads to the acceleration of the ions toward the sample and thus to the sputtering of the sample. Neutral particles are thereby released from the sample in the case of conductors, semiconductors and nonconductors. These neutral particles flying toward the mass analyzer are ionized in the plasma and examined for their mass in the mass analyzer. To switch from DBM/SNMS operation to SBM/SNMS operation, it is necessary only to reduce the voltage difference between plasma and sample to such an extent that ions from the plasma will no longer excite or sputter the sample, and to perform the bombardment of the sample with the ion source. The mean free length of travel of the primary ions is so great that the primary ion current is able to pass through the plasma largely undisturbed. Neutral particles released out by the ion bombardment are ionized by the plasma and analyzed in the mass analyzer.

The invention is based substantially on the discovery that, in the SBM/SNMS method it is not necessary to prevent excessive loading of the sample by plasma particles by using an electrical diaphragm. Simply a suitable setting of the plasma potential suffices for this purpose. Also, the suppression of secondary ions with a diaphragm is not necessary, since usually the number of neutral particles emitted is considerably greater than the number of secondary ions emitted. Moreover, the directly released out secondary ions and the neutral particles ionized afterward have different energy distributions, so that the secondary ions can be suppressed by means of an ion lens in front of the mass analyzer (setting an energy window).

On the basis of the favorable arrangement of the ion source, detection system and sample with respect to one another, a large solid angle of the sputtered neutral particles, in comparison with the previously known arrangement, is covered by the detection system. This leads to a high sensitivity of detection. In this manner also, in the proposed apparatus an ion gun with a low primary ion current can be used, such as for example a fine-focusing ion source, which can be used for microanalysis. SNMS microanalyses are possible with a lateral resolution of 1 micrometer. This applies to metals, semiconductors and nonconductors. In the case of nonconductors, the charge produced by the ion bombardment of the sample is compensated by the electron component of the plasma, since the sample has direct contact with the plasma.

Another decided advantage of the apparatus according to the invention lies in the fact that it is suitable also for the performance of the SIMS method without special conversion. In the SIMS method (secondary ion mass spectrometry) a sample is bombarded with ions. The secondary ions knocked out directly by this ion bombardment are examined for their mass. Basically, SIMS could also be performed with the apparatus previously disclosed in DE-OS No. 29 50 330. In comparison to an "ideal" SIMS configuration, however, this would be possible only with great losses of sensitivity (several orders of magnitude). A vertical bombardment of the sample with simultaneous analysis, as is necessary for a high dynamic and good depth resolution in the case of depth profiles, cannot be performed, either, with the previously described apparatus. This applies not only to SIMS analyses but also to SNMS analyses. Lastly, neither can microanalyses be performed for reasons of intensity.

For the performance of the SIMS method with the apparatus according to the invention, it is necessary only to shut off the radiofrequency plasma. The sample can then be analyzed by the SIMS method under optimum conditions. As in the case of SNMS operation, SIMS microanalyses can also be performed.

With the plasma shut off, secondary electron photographs can be made in the sub-micron range by excitation from a fine focusing ion source. The detector required for this purpose can be placed on the detection side and protected against sputtering by a mask in the case of plasma operation.

Direct SIMS-SNMS comparative measurements have not been possible in the past under optimum conditions (i.e., with a high sensitivity of detection in both processes). They have always required different measuring instruments or at least extensive alterations. SIMS-SNMS comparative measurements, however, are often highly desired, since these two spectroscopic methods complement one another. With the SNMS process, quantitative determinations of the composition of the sample are possible. On the other hand, in the SIMS method, the formulation of secondary ions of the sample surface depends in a complex manner on the matrix of the surface, so that sensitivity variations of several orders of magnitude can occur. With the SIMS method, therefore, highly sensitive analysis are often possible, but not quantitative analyses. Secondary ion spectra can supply chemical information (e.g., on binding and binding states) on the basis of the above-mentioned matrix dependency of the secondary ion emission.

The direct performance of comparative SIMS-SNMS measurements is possible with the apparatus of the invention because the sample can be brought to a position which is most favorable both for SIMS as well as for both types of SNMS operation. The SBM/SNMS method can be performed with a higher detection sensitivity than the state of the art given by DE-OS No. 20 50 330, since the diaphragm defining the solid angle is eliminated. Furthermore, the distance between the sample and the detection system can be at least halved in comparison to the previously published arrangement. In the case of DBM, of course, this also reduces the probability of post ionization again by about half. But the number of sputtered particles hitting the aperture of the ion lens is about four times greater. This is the case even without considering the limitation of the solid angle by the electrical diaphragm. All in all, for all of the methods of measurement referred to above, the result is the best geometrical arrangement for the attainment of maximum performance data. A quick change between SIMS and SNMS as well as between both kinds of SNMS operation can now be achieved by a simple changeover.

In accordance with the invention, apparatus for performing the SNMS process comprises a separate ion source, a sample holder means including a chamber producing a radio-frequency plasma, and a mass analyzer, the ion source and the mass analyzer being arranged side by side on the same side of the chamber for the radio-frequency plasma, and a sample mounted on the sample holder being situated within the chamber for the radio-frequency plasma.

Further advantages and details of the invention are to be explained with the aid of embodiments represented in FIGS. 1 to 3.

BRIEF DESCRIPTION OF THE DRAWINGS

FIG. 1 is a schematic sectional view of a combination SIMS-SNMS apparatus;

FIG. 2 is a schematic sectional view of the sample holder of FIG. 1 on a larger scale; and FIG. 3 is a schematic sectional view of an additional sample holder.

DESCRIPTION OF PREFERRED EMBODIMENTS

The apparatus represented in FIG. 1 has in its center the plasma vessel 1 which is surrounded by a single-turn radio-frequency coil 2 consisting of a strip of flat metal. The control of the plasma 5 produced in the inner chamber 4 and indicated by the pattern of dots is performed by means of a probe 3.

The plasma vessel 1 is equipped with lateral flanges 6 and 7. A sample entrance lock 8 is mounted on the flange 6. This lock comprises the lock base body 9, the valve 10 and an intermediate chamber 11 which is connected by the opening 12 in flange 6 to the inner chamber 4 of the plasma vessel 1. Through the lock base body 9, the intermediate chamber 11 and the opening 12 in flange 6 extends the sample rod 13 shown in the position for measurement, on which the sample 14 is mounted. The sample holder generally represented by 15 is shown on a larger scale in FIG. 2. The connections 16 and 17 on the lock base body 9 and 18 on the intermediate chamber 11 serve for the connection of vacuum pumps. Additional connections 19 and 20 on flange 6 serve respectively for the measurement of pressure and the admission of a working gas, preferably argon, for the plasma 5.

On the opposite side of the plasma vessel 1 a casing 21 for a mass spectrometer is fastened to flange 7. The mass spectrometer comprises a quadrupole mass filter 22 in front of which is an ion lens 23 extending through the flange 7 with its entrance aperture reaching all the way to the plasma 5, for the placement of an energy window. In back of the quadrupole 22 is another ion lens 24 which deflects the ions which are to be registered to an axially offset multiplier 25. The casing 21 is equipped with the connection 26 for the attachment of a high-vacuum pump. The evacuation of the inner chamber 4 of the plasma vessel 1 is performed by the vacuum pumps attached to the connections 18 and 26.

Lock 8, plasma vessel 1, ion lens 23 and quadrupole 22 are disposed equiaxially. The axis of the entire system is generally designated by 27.

In addition to the mass spectrometer, an ion gun 28 is mounted to the casing 21. This is arranged such that its focal point is on the sample 14 in its position of measurement as represented. The sample can be mounted for tilting (arrow 29) so that it can be aligned perpendicular to the direction of the impinging ions.

Furthermore, a secondary electron detector 30 is mounted on the flange 7. It can be made displaceable so that it will be in its measuring position only in the case of the recording of secondary electron images. In plasma operation it is withdrawn and protected against sputtering by means of a mask which is not shown.

FIG. 2 shows the configuration of the sample end of the sample rod 13. On it is a sample holder 31, on which the sample 14 is fastened by a clamp which is not shown. A supply of coolant for the inner chamber 33 of the sample holder 31 is delivered through one inlet and two outlet lines 32. The lines 32 as well as the mountings 34 of the sample holder 31 comprise electrically insulating material, so that the sample holder 31 and with it the sample 14 can be set at a specific potential.

With the sample 14 there is also associated a cap 35 with a bombardment opening 36, which is displaceable axially. This displaceable cap has the purpose of permitting a uniform ablation of the sample (Appl. Phys. 20 (1979), pp. 55–60).

The sample surface can be tilted (e.g., perpendicular to the impinging ion beam or parallel to the aperture of the ion lens). An example of this is shown in FIG. 3. The sample holder 31 includes for this purpose a dome 41 with a correspondingly shaped component 42 sliding thereon, on which the sample 14 is mounted. The component 42 also bears the cap 35 on a ceramic ring 43.

To analyze a sample 14 by the DBM/SNMS method with the apparatus represented in FIG. 1, the one-turn coil 2 is supplied with current in a known manner such that the plasma 5 is formed. The ion gun 28 is shut off. The sample 14 and its sample holder 31 are applied to such a potential (e.g., some 10 volts to a few kilovolts) that the ions of the plasma 5 strike the sample 14. In the direct bombardment mode, a DC voltage, and in the case of insulators a radio-frequency AC voltage, is applied. Neutral particles thus formed, and flying in the direction of the ion lens 23, are ionized and separated according to their mass in the connected mass spectrometer 22.

If the sample is to be tested immediately thereafter by the SBM/SNMS method, first it is necessary to reduce the potential difference between sample 14 and plasma 5 such that ions of the plasma either will no longer reach the sample or will strike it only with such low energy that neutral particles or secondary ions will no longer be emitted. Furthermore, the ion gun 28 is to be placed in operation. The sample is bombarded by means of ions produced therein, e.g., 1 to 5 keV argon ions. The sputtered neutral particles flying in the direction of the ion lens 23 are ionized in the plasma 5 and analyzed in the mass spectrometer. To separate the undesired secondary ions from the desired neutral particles ionized by the plasma 5 on their way to the ion lens 23, an energy window is set by means of the ion lens 23. This measure suffices to suppress undesired secondary ions, since they have different energy distributions, as a rule, from the desired neutral particles.

Lastly, the sample 14 can be analyzed by the SIMS process by means of the apparatus according to the invention, in the measurement position represented. For this purpose it is necessary, starting out from the SBM/SNMS process, to interrupt the current in the winding 2 and thus to extinguish the plasma. The plasma can also be extinguished by interrupting the supply of the working gas. By bombardment with ions from the ion gun 28, secondary ions are released from the sample 14. Secondary ions flying in the direction of the ion lens 23 are analyzed for mass in the spectrometer that follows. With the secondary ion lens, an energy window suitable for SIMS analysis is set.

In previously known arrangements, microanalysis by means of finely focusing ion sources is hardly possible on account of the more unfavorable transmission conditions, since the achievable absolute ion currents in such ion sources are lower by several orders of magnitude than the large-area ion guns utilized in the SNMS measurements performed heretofore. In the embodiment represented, the sample is in the most favorable position as regards transmission, both for SNMS measurements and for SIMS measurements, so that the use of fine-focusing ion guns with low current provides substantially better results than formerly. Lastly, secondary electron pictures can be taken with the fine-focusing ion source and the secondary electron detector 30. For this variant kind of measurement, the individual components also have a favorable arrangement with respect to one another.

In comparison with the formerly known apparatus, in the present system the solid angle definition by the diaphragm is eliminated, and the aperture of the ion lens is better filled out by the sputtered particles. The gain in intensity thereby achieved for SIMS and DBM/SNMS amounts to approximately two orders of magnitude. Only one sample transfer system is required for all possible analyses.

Another important advantage is achieved in the testing of samples of electrically insulating material. Samples of this kind have the disadvantage, in analysis by the formerly known SBM/SNMS method, that they are charged up by the ion bombardment. To prevent this, the additional use of electron guns for charge compensation is known. The charge compensation can also be accomplished by extraction of plasma electrons by means of the electrical diaphragm. In working with the apparatus according to the invention, this is not necessary, since the sample is located within the plasma and its charging is prevented by the electrons present in the plasma.

With the apparatus described, a great variety of analyses and ablation conditions can be applied in combination with one another or successively, e.g.:

high rates of ablation by DBM (by applying a sample potential in the case of conductive samples, or by RF sputtering, for example, in the case of insulators), followed by a static SIMS or SNMS analysis in DBM;

high rates rates of ablation by DBM followed by a microanalysis of the bombardment crater.

These two examples show that the apparatus configuration proposed by the invention, in comparison to previously known SNMS arrangements, permits completely novel analytical experiments, inasmuch as the recording of secondary electron images is possible at any time without reconstruction. For this purpose the electron detector 30 is brought into its working position and turned on. With ions from the ion source 28, whether or not it is configured as a finely focused ion source, the sample is scanned in a raster. Secondary electrons thus formed are registered by the detector 30 and provide a picture of the surface of the sample.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Apparatus for performing the SNMS process, comprising:
   a separate ion source, a sample holder, means including a chamber for producing a radio-frequency plasma, and a mass analyzer, said ion source and said mass analyzer being arranged side by side on the same side of said chamber for the radio-frequency plasma, said sample holder being for mounting a sample situated within said chamber for the radio-frequency plasma.

2. Apparatus according to claim 1, including an ion lens for the setting of an energy window and placed in front of said mass analyzer.

3. Apparatus according to claim 1, including a secondary electron detector diposed beside said ion source and said mass analyzer.

4. Apparatus according to claim 1, in which said sample holder includes a displaceable sample rod which is disposed on the side of said chamber for the radio-frequency plasma that is opposite said mass analyzer.

5. Apparatus according to claim 1, in which said chamber for the radio-frequency plasma comprises an RF-permeable, highly vacuum-tight vessel which is surrounded by a one-turn RF coil.

6. Apparatus according to claim 5, in which said plasma vessel is of cylindrical configuration and has two flanges at its ends, and which includes a sample transfer system fastened to one of said flanges on the one side of said vessel and in which said mass analyzer and said ion source are fastened to the other of said flanges on the other side of said vessel.

7. Apparatus according to claim 1, in which said mass analyzer includes a quadrupole mass filter.

8. Apparatus according to claim 1, in which said ion source is a fine-focus ion source for the performance of microanalyses.

9. Apparatus according to claim 1, in which said sample holder is capable of mounting the sample tiltably on said sample holder.

* * * * *

UNITED STATES PATENT AND TRADEMARK OFFICE
CERTIFICATE OF CORRECTION

PATENT NO. : 4,670,651

DATED : June 2, 1987

INVENTOR(S) : Stefan Meier, et al.

It is certified that error appears in the above-identified patent and that said Letters Patent is hereby corrected as shown below:

Column 7, line 19 for "diposed" read -- disposed --.

Signed and Sealed this

Twenty-second Day of August, 1989

Attest:

DONALD J. QUIGG

Attesting Officer

Commissioner of Patents and Trademarks